(12) United States Patent
Angelsen et al.

(10) Patent No.: US 8,157,739 B2
(45) Date of Patent: Apr. 17, 2012

(54) ULTRASOUND IMAGING WITH SYNTHETIC RECEIVE APERTURE AND WIDE APERTURE, FOCUSED TRANSMIT BEAM

(75) Inventors: Bjørn A. J. Angelsen, Trondheim (NO); Tonni F. Johansen, Trondheim (NO)

(73) Assignee: SURF Technology AS, Trondheim (NO)

( * ) Notice: Subject to any disclaimer, the term of this patent is extended or adjusted under 35 U.S.C. 154(b) by 956 days.

(21) Appl. No.: 10/932,871

(22) Filed: Sep. 2, 2004

(65) Prior Publication Data

US 2005/0054929 A1 Mar. 10, 2005

Related U.S. Application Data

(60) Provisional application No. 60/499,485, filed on Sep. 2, 2003.

(51) Int. Cl.
*A61B 8/00* (2006.01)
*A61B 8/14* (2006.01)

(52) U.S. Cl. .......................... 600/447; 600/437; 600/466

(58) Field of Classification Search .................. 600/407, 600/437–439, 447–449; 601/2–4; 310/314–317; 367/117–130
See application file for complete search history.

(56) References Cited

U.S. PATENT DOCUMENTS

| | | | | |
|---|---|---|---|---|
| 4,576,045 A * | 3/1986 | Miller-Jones | .................... | 73/626 |
| 4,759,372 A * | 7/1988 | Umemura et al. | ............. | 600/447 |
| 4,917,097 A * | 4/1990 | Proudian et al. | .............. | 600/463 |
| 5,186,177 A * | 2/1993 | O'Donnell et al. | ........... | 600/463 |
| 5,226,847 A * | 7/1993 | Thomas et al. | ............... | 600/463 |
| 5,276,654 A * | 1/1994 | Mallart et al. | ..................... | 367/7 |
| 5,476,098 A * | 12/1995 | O'Donnell | ..................... | 600/447 |
| 5,522,393 A * | 6/1996 | Phillips et al. | ................. | 600/455 |
| 5,590,659 A * | 1/1997 | Hamilton et al. | ............. | 600/447 |
| 5,617,862 A * | 4/1997 | Cole et al. | ..................... | 600/459 |
| 5,817,024 A * | 10/1998 | Ogle et al. | ..................... | 600/447 |
| 5,893,363 A * | 4/1999 | Little et al. | ..................... | 600/447 |
| 5,924,993 A * | 7/1999 | Hadjicostis et al. | .......... | 600/462 |
| 5,935,072 A * | 8/1999 | Hamilton et al. | ............. | 600/447 |
| 5,947,905 A * | 9/1999 | Hadjicostis et al. | .......... | 600/463 |
| 5,951,479 A * | 9/1999 | Holm et al. | .................... | 600/447 |
| 5,964,709 A * | 10/1999 | Chiang et al. | ................. | 600/447 |
| 5,967,984 A * | 10/1999 | Chu et al. | ...................... | 600/439 |
| 5,980,458 A * | 11/1999 | Clark | ............................. | 600/437 |
| 5,993,393 A * | 11/1999 | Ryan et al. | ..................... | 600/463 |
| 6,029,116 A * | 2/2000 | Wright et al. | .................... | 702/32 |
| 6,066,099 A * | 5/2000 | Thomenius et al. | .......... | 600/447 |
| 6,203,498 B1 * | 3/2001 | Bunce et al. | ................... | 600/446 |
| 6,254,542 B1 * | 7/2001 | Hamilton et al. | ............. | 600/447 |
| 6,271,620 B1 * | 8/2001 | Ladabaum | .................... | 310/334 |
| 6,471,651 B1 * | 10/2002 | Hwang et al. | ................. | 600/459 |

(Continued)

OTHER PUBLICATIONS

Matthew O'Donnell et al., Efficient synthetic aperture imaging from a circular aperture with possible application to catheter-based imaging, IEEE Transactions on Ultrasonics, Ferroelectrics, and Frequency Control, vol. 39, No. 3, May 1992.*

*Primary Examiner* — Long V. Le
*Assistant Examiner* — Angela M Hoffa
(74) *Attorney, Agent, or Firm* — Cozen O'Connor

(57) ABSTRACT

A method and an instrument for ultrasound imaging using an array of transducer elements which is connected to the instrument with a limited number of wires, where focusing of the transmit beam improves image signal to noise ratio above state of the art methods. This allows the use of higher ultrasound frequencies providing improved image resolution.

7 Claims, 4 Drawing Sheets

U.S. PATENT DOCUMENTS

| | | | |
|---|---|---|---|
| 6,508,764 B1 * | 1/2003 | Thiele et al. | 600/437 |
| 6,540,677 B1 * | 4/2003 | Angelsen et al. | 600/437 |
| 6,736,780 B2 * | 5/2004 | Song et al. | 600/447 |
| 2002/0139193 A1 * | 10/2002 | Angelsen et al. | 73/602 |
| 2003/0163046 A1 * | 8/2003 | Nohara et al. | 600/443 |
| 2004/0147841 A1 * | 7/2004 | McLaughlin et al. | 600/437 |
| 2005/0203396 A1 * | 9/2005 | Angelsen et al. | 600/437 |

* cited by examiner

ULTRASOUND IMAGING WITH SYNTHETIC RECEIVE APERTURE AND WIDE APERTURE, FOCUSED TRANSMIT BEAM

CROSS REFERENCE TO RELATED APPLICATION

This is application claims priority from U.S. Provisional Patent Application Ser. No. 60/499,485 filed Sep. 2, 2003.

FIELD OF THE INVENTION

The present invention is directed to methods of ultrasound imaging using synthetic aperture for the receive beam, with a wide aperture, focused transmit beam. The methods have special applications in situations where the aperture is an array of elements, and it is a limited number of electrical wires available for control of the array.

An important example is medical ultrasound imaging where the transducer array is mounted at the distal tip of an elongated device for insertion into the body, for example a catheter or an endoscope, with electric wires along the device that connects the array to an external ultrasound imaging instrument.

The method allows the use of a reduced number of wires, down to a two wire cable, to connect the array at the tip of such a device and the external imaging instrument. This allows use of very thin elongated devices and also reduces the cost of the device that opens for the use of disposable devices.

DESCRIPTION OF THE RELATED ART

There exists methods and devices where switching circuits are placed near the ultrasound transducer array, that allows connecting the individual array elements to the external imaging instrument in a sequence, for example as described in U.S. Pat. No. 4,917,097. The ultrasound image is reconstructed from the signals from the individual elements with synthetic aperture techniques known to anyone skilled in the art.

There further is proposed methods, U.S. Pat. No. 5,186,177, where a selectable group of the elements are used to transmit ultrasound pulses, while the signal is received from individual elements or groups of elements, and the final image is reconstructed with synthetic aperture and filtering techniques known to anyone skilled in the art. In U.S. Pat. No. 5,226,847 is disclosed a system with omni-directional transmission of ultrasound with synthetic aperture image construction from the received individual element signals.

SUMMARY OF THE INVENTION

For best possible resolution in the image, one wants to use as high as possible ultrasound frequency. The maximal ultrasound frequency is limited by the signal to noise ratio, where imaging techniques that provides the maximally possible signal to noise ratio hence allows the use of the highest ultrasound frequency and hence gives the best possible resolution.

The present invention presents a method that gives the maximally possible receive signal to noise ratio for a given aperture, and hence allows the use of the highest possible frequency with the best possible resolution in the ultrasound image.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE PRESENTLY PREFERRED EMBODIMENTS

Figure 1:
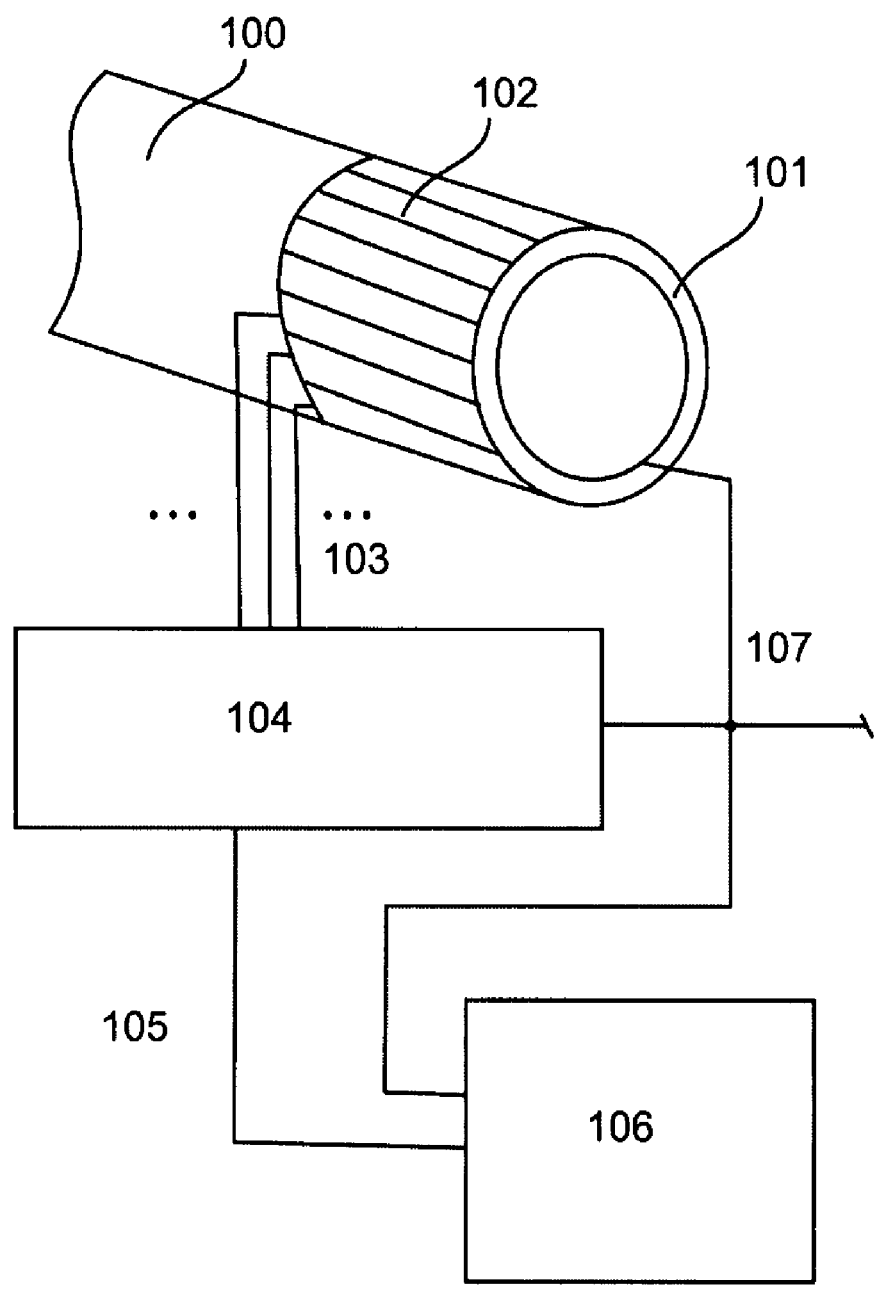
FIG. 1 shows example of method for synthetic aperture imaging using circular array.

FIG. 1 shows by way of example a state of the art method of synthetic aperture imaging with a circular array 101 from the tip of a catheter 100. The array elements 102 are via conductors 103 connected to a multiplexing circuit 104 that connects in a sequence one element to the conductor 105 that connects the element to an external imaging instrument 106. The element can be selected via external addressing of the multiplexer, or the multiplexer address can be changed internally in increments for each set of transmit pulses. One side of the transducer elements has a common ground that connects via a wire 107 to the common ground of the instrument and the multiplexer.

The image is built up from the signal from M neighboring elements with the known synthetic aperture technique. Suppose the signal to noise ratio for the individual elements is $S_1/N_1$. In the synthetic aperture processing where the signal from M elements are combined coherently in phase, the signal power increases by $M^2$ to $S_M = M^2 * S_1$ from the coherent summation. The noise power increases by incoherent summation to $N_M = M * N_1$. The signal to noise ratio in the synthetic aperture image where M elements are combined for each point, is therefore $$\frac{S_M}{N_M} = M \frac{S_1}{N_1} \qquad (1)$$

If the transmit pressure amplitude in an image point is increased by a factor K, the signal power for each element from this image point increases by a factor $K^2$, without any increase in the noise power. Focusing the transmit beam from K elements onto a point, gives such an increase of the focal pressure amplitude by a factor K, which gives a signal to noise ratio for scatterers in the transmit focus, where the image is reconstructed with a synthetic aperture receive beam for M elements of $$\frac{S_{KM}}{N_{KM}} = K^2 M \frac{S_1}{N_1} \qquad (2)$$

Hence, as signal to noise ratio increases by the square factor $K^2$ of the number of K focused transmit elements, the wide aperture focusing of the transmit beam gives a strong increase in the signal to noise ratio, allowing for an increase in the ultrasound frequency with subsequent improvement in image resolution.

Figure 2A:
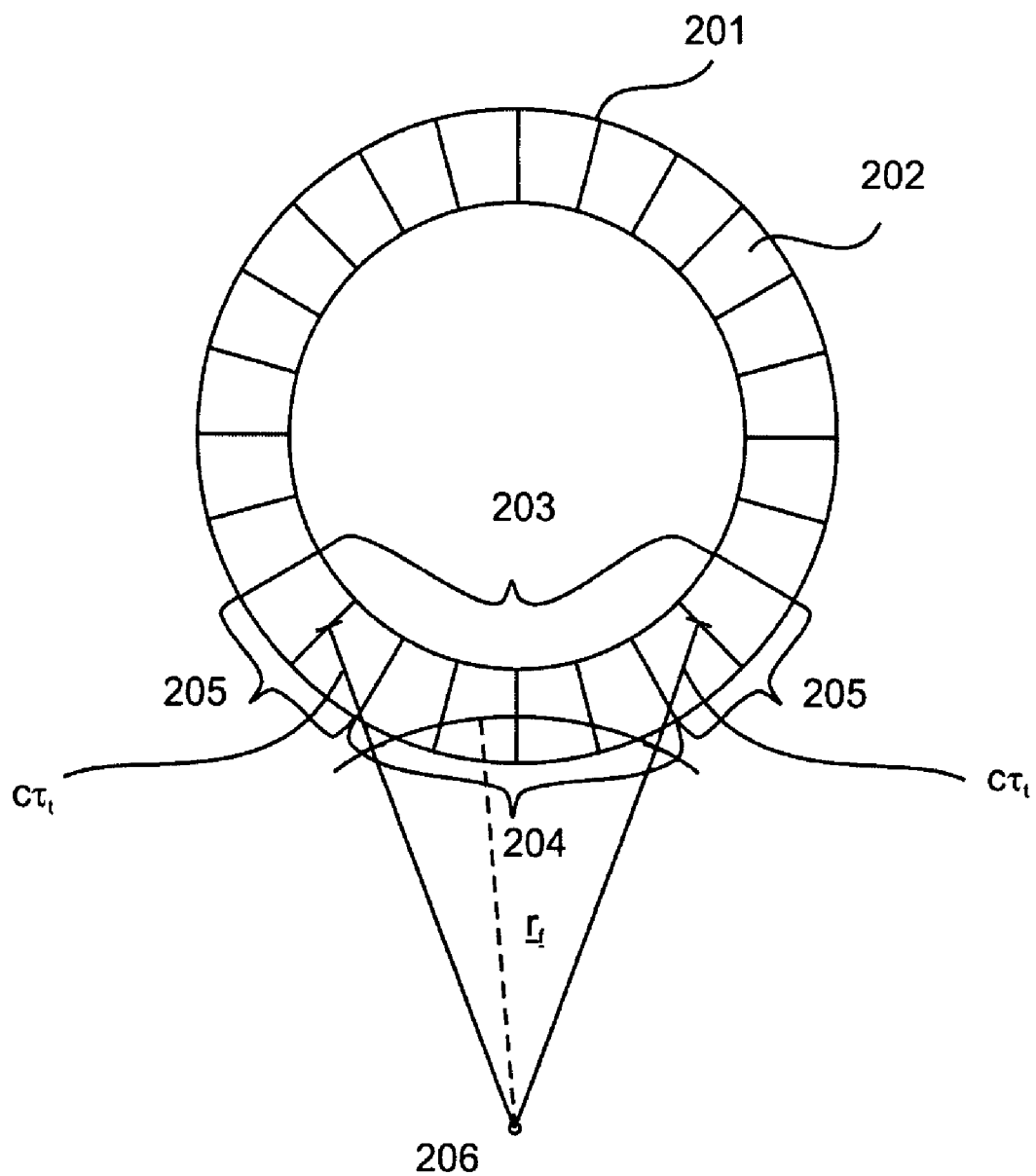
FIGS. 2a-b, show sketch of method of focusing and electronic control of circular array with wide transmit aperture.

FIG. 2a gives an example embodiment according to the invention, where 201 shows by example a circular array with elements 202. The transmit beam is generated by the group 203, which is for this particular example further subdivided into a central group 204 and a group 205 of elements of each side. To focus the transmit beam onto a point $r_f$, 206, the pulse from the outer group 205 of elements is transmitted a time $\tau_t$ before the pulse from the central group 204 of elements, so that the pulse from the two groups arrive at the same time at the focal point 206. The width of the groups is selected so narrow that the beam from each group covers the focus well. For wider transmit apertures one can divide the aperture into more subgroups, to obtain so narrow width of each group that the radiation diagram from all groups covers the focus.

Figure 2B:
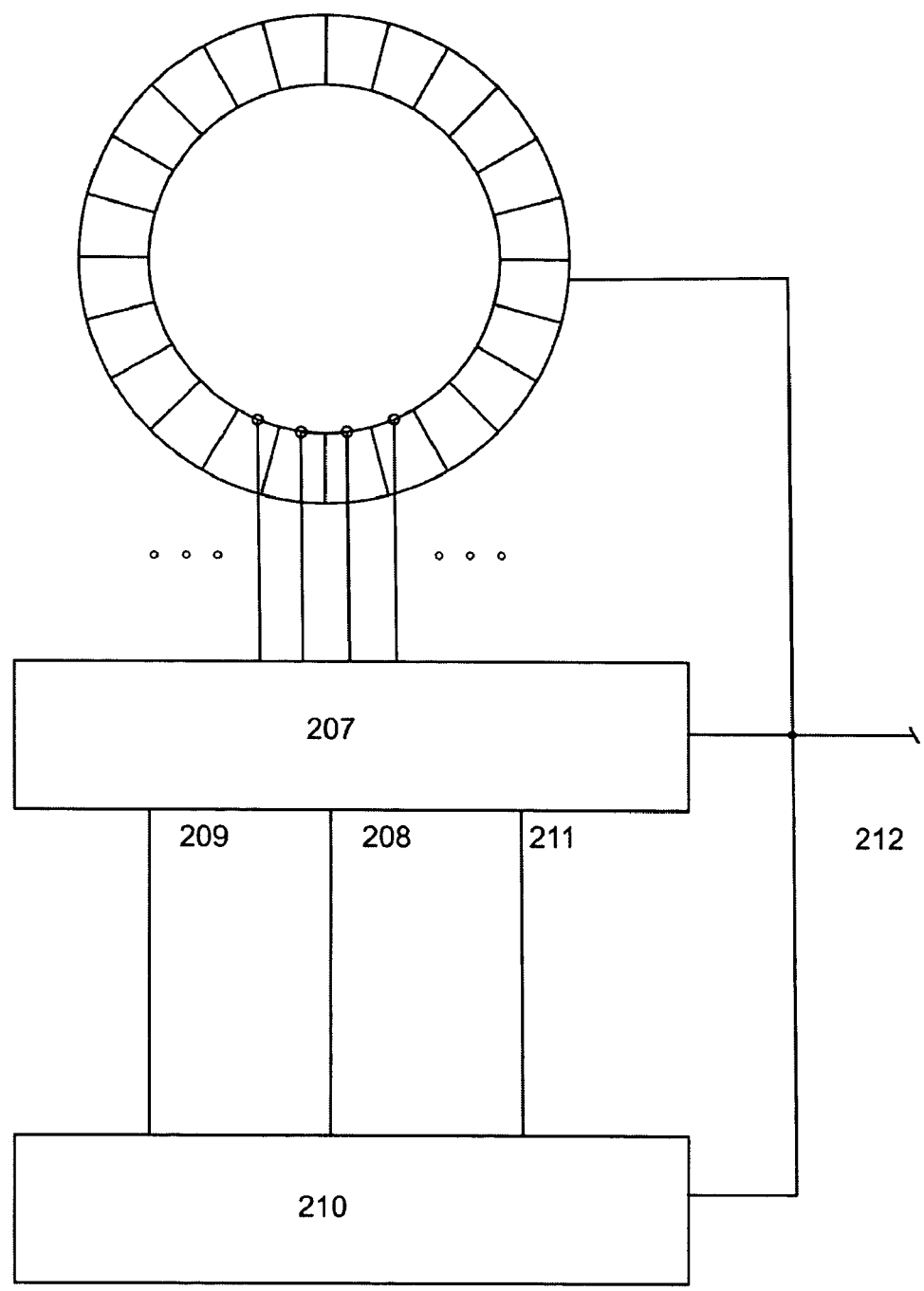

According to this embodiment of the invention, as shown in FIG. 2b, all elements of the circular array is connected to a switching circuit 207, that connects $K_1$ central elements of the aperture to a single wire 208, and $K_2$ elements on each side to a second wire 209, where $K=K_1+K_2$ is the total number of elements in the transmit aperture. The two wires 208 and 209 can be connected directly to the imaging instrument 210 so that the drive pulses with their interdelay is generated in the imaging instrument. In addition, the active element of the receive aperture is connected by the switching circuit 207 to the wire 211 that couples the signal from this element to the imaging instrument 210. A common ground of the elements and the switching circuit is connected to the ground of the imaging instrument 210 via the wire 212. In addition to the connecting wires that is shown, one can typically also have wires that provide power for the switching circuit, and address signals for the switching circuit. The switch addressing can also be transferred from the imaging instrument via the pulsing lines 208 or 209, for example with an increment in the switch address for each transmit pulse, or each group of transmit pulses.

Switching the active transmit aperture in a sequence around the array in steps of one element at the time, one will in a sequence receive back-scattered signals from all elements with a focused transmit beam. The image can then be reconstructed with the known synthetic aperture receive beam forming. To increase receive signal to noise ratio, one can also connect several elements around the center of the transmit aperture. Lateral filtering of the received signal from several receive element groups can then be done to improve lateral resolution in the image, according to known techniques.

Figure 3:
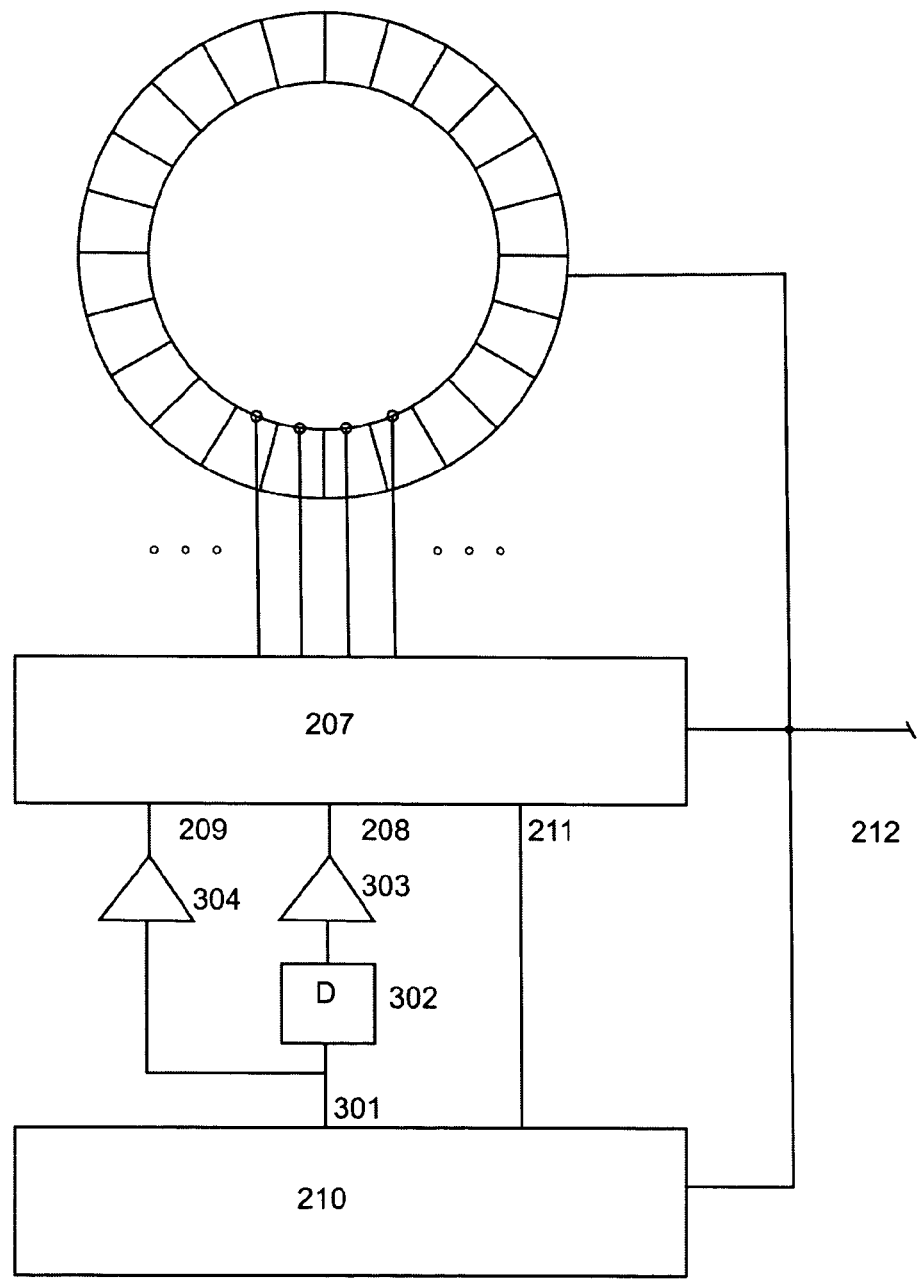
FIG. 3 shows example of reduced number of cables between a catheter tip and an imaging instrument by adding electronics at the imaging tip.

The number of wires connecting the imaging array and the imaging instrument can be further reduced with the system in FIG. 3, where the transmit pulse is transmitted from the imaging instrument over the wire 301, and for the central group of elements the pulse is delayed an adequate time in the circuit 302 that drives the central elements 204 of the transmit aperture via the wire 208, possibly through a drive amplifier 303 that can be missing depending on the electrical impedance of the central group 204 in the actual situation. The transmit wire 301 connects directly to the outer group of elements 205 in the transmit aperture via the wire 209, possibly through the transmit amplifier 304 that also can be missing, depending on the electrical impedance of the actual transmit aperture.

The receive wire 211 could also be connected to the wire 301 through a transmit/receive switching circuit according to known methods, to reduce the number of wires connecting between the imaging array and the imaging instrument. The receive elements could also be the same as the central group of transmit elements, where the receive signal would also be found on 208, and connected to 301 via a transmit receive switch according to known methods.

The length of the wires between the circuits and the imaging instrument are substantial compared to the wavelength at higher frequencies (above ~10 MHz), from $\lambda/4$ to several $\lambda$. To avoid signal power losses in the wires and maintain a good signal to noise ratio at the higher frequencies it is advantageous to place receiver amplifiers on the circuit close to the array, so that amplified signals are transmitted on the wires. To minimize the number of wires connecting the array and the imaging instrument, it is further advantageous to apply some beam forming electronics at the imaging tip. Grouping a set of neighboring elements together and moving the group along the array in steps of one array element, is one interesting beam forming technique that has advantages in signal to noise ratio above the single element synthetic aperture technique. It is further interesting to apply signal delays to the element signals at the circuit for electronic focusing and direction steering of the beam.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

We claim:

1. A method for ultrasound imaging using an array of ultrasound transducer elements, said method comprising the steps of:

selecting, in a transmit mode, at least two transmit groups of elements from the transducer elements for transmitting ultrasound pulses with a delay between the transmit pulses of each of the at least two transmit groups so that the pulses of said at least two transmit groups arrive at the same time at a transmit beam focus and form together a full transmit aperture for a focused ultrasound transmit beam with a selectable focus distance, the elements of each of the at least two groups of elements being arranged symmetrically around an axis of said focused transmit beam, the focus distance being selectable by varying the delays of the at least two transmit groups;

scanning the focused transmit beam laterally by selecting different transmit groups from the transducer elements;

for each focused transmit beam, transmitting a sequence of M sets of ultrasound pulses of the each focused transmit beam, where each of the M sets of ultrasound pulses includes the ultrasound pulses of the at least two transmit groups of the each focused transmit beam;

forming a set of M neighboring receive groups of elements for each sequence of M sets of ultrasound pulses of the each focused transmit beam, wherein each one of the M neighboring receive groups is formed in response to a respective one of the M sets of ultrasound pulses of the each focused transmit beam by connecting hot electrodes of the each of the receive groups of elements electrically together and storing the received signal from the each of the receive groups, and wherein the total of the M receive groups for the each focused transmit beam span a receive aperture;

combining the received stored signals from the M neighboring receive groups for said each focused transmit beam to construct focused receive signals in a range around the selected transmit focus along the axis of said each focused transmit beam; and forming an ultrasound image using focused receive signals for multiple selected transmit focus distances and/or multiple selected transmit beam directions.

2. The method of ultrasound imaging according to claim 1, wherein said step of forming an ultrasound image includes using a synthetic aperture technique.

3. The method of ultrasound imaging according to claim 2, wherein the synthetic aperture technique includes lateral filtering of the signals.

4. An ultrasound imaging instrument, comprising, an array of ultrasound transducer elements, each of said transducer elements having a hot electrode;

a switching circuit connected to the hot electrode of each of said transducer elements; and a transmit circuit, a receive circuit including receive beam focusing means, and image forming means, said switching circuit being configured to connect, in a transmit mode, at least two transmit groups of elements from the transducer elements to said transmit circuit, said transmit circuit being configured to drive each of said at least two transmit groups with pulses having time delays between the pulses for each of said at least two groups so that the pulses from the total of said at least two transmit groups of elements arrive at the same time at a transmit beam focus and form together a full transmit aperture for a focused ultrasound transmit beam with selectable focus distance, the elements of each of the at least two groups of elements being arranged symmetrically around an axis of said focused transmit beam, the selectable focus distance being selected by varying said delays for said transmit groups, and said switching circuit being further configured to scan said focused transmit beam laterally with respect to a surface of the array by selecting different transmit groups from said transducer elements, said switching circuit being configured to connect, in a receive mode, a receive group of elements to the receive circuit, said receive group containing one or more elements selected from said transducer elements, said receive circuit being configured to amplify, digitize, and store a signal received by said receive group of elements, said transmit circuit being further configured to drive the selected transmit groups for each focused transmit beam to transmit a sequence of M sets of ultrasound pulses of the each focused transmit beam, each of the each of the M sets of ultrasound pulses including the ultrasound pulses of the at least two transmit groups of the each focused transmit beam, and for each said sequence of M sets of transmit pulses said switching circuit being configured to successively connect a set of M neighboring receive groups of elements to said receive circuit so that each one of the M neighboring receive groups is formed in response to a respective one of the M sets of ultrasound pulses of the each focused transmit beam, and so that the total of said M receive groups span a receive aperture, said receive circuit being further configured to combine the received stored signals from said M receive groups of said each focused transmit beam and construct focused receive signals in a range around said selected transmit focus along the axis of said each focused transmit beam, and said image forming means being configured to form an ultrasound image using the focused receive signals from at least one of a plurality of selected transmit focus distances and a plurality of selected transmit beam directions.

5. An ultrasound imaging instrument according to claim 4, wherein said array is curved around the tip of an elongated device.

6. An ultrasound imaging instrument according to claim 5, wherein said switching circuit, transmit circuit, and receive circuit are included in an integrated circuit mounted close to the transducer array at the tip of said elongated device.

7. An ultrasound imaging instrument according to claim 5, where said elongated device is a catheter.

* * * * *